United States Patent [19]
Danheiser et al.

[11] Patent Number: 5,004,815
[45] Date of Patent: Apr. 2, 1991

[54] METHOD FOR SYNTHESIZING β-LACTONES AND ALKENES

[75] Inventors: Rick L. Danheiser, Watertown; James S. Nowick, Cambridge, both of Mass.

[73] Assignee: Massachusetts Institute of Technology, Cambridge, Mass.

[21] Appl. No.: 343,909

[22] Filed: Apr. 26, 1989

[51] Int. Cl.⁵ .............................................. C07D 305/12
[52] U.S. Cl. .................................... 549/328; 549/214; 549/332
[58] Field of Search ........................ 549/328, 214, 332

[56] References Cited

PUBLICATIONS

J. Wemple, *Tetrahedron Letters* No. 38:3225–3258 (1975).
W. Adam and H. Fick, *Journal of Organic Chemistry* 43(24):4574–4577 (1978).
W. Adam et al., *Journal of the American Chemical Society* 94:2000–2006 (1972).
D. Seebach and R. Haner, *Chemistry Letters*, pp. 49–52 (1987).
D. J. Dagli et al., *Journal of Organic Chemistry* 40:3173–3178 (1975).
W. Adam and L. A. A. Encarnacion, *Synthesis*, pp. 388–390 (1979).
S. Musamune et al., *Journal of the American Chemical Society* 98:7874–7875 (1976).

*Primary Examiner*—Richard L. Raymond
*Assistant Examiner*—Ba K. Trinh
*Attorney, Agent, or Firm*—Hamilton, Brook, Smith & Reynolds

[57] ABSTRACT

β-Lactones are synthesized from a thiol ester and a ketone by a method which efficiently produces β-lactones in high yields. The method involves combining the thiol ester, a ketone or aldehyde, a base, and an organic solvent at subambient temperatures. The thiol ester and ketone form an adduct, which upon warming, spontaneously cyclizes to yield a β-lactone. β-Lactones formed by this method are then decarboxylated, generally by warming in the presence of an adsorbent in an organic solvent, to stereospecifically form the corresponding alkenes.

24 Claims, 4 Drawing Sheets

METHOD FOR SYNTHESIZING β-LACTONES AND ALKENES

The Government has rights in this invention pursuant to grant No. DHE-831546 awarded by the National Science Foundation and grant No. 5-R01-GM28273-10 awarded by the National Institutes of Health.

BACKGROUND

A number of methods have been developed for the stereoselective synthesis of substituted alkenes (olefins). β-Lactones (also known as 2-oxetanones) are known to decompose at moderate temperatures into alkenes and carbon dioxide. This thermal lability imparts to the oxetanone ring system a unique property for serving as an alkene precursor. However, the synthesis of alkenes from β-lactones has not been widely utilized due to the lack of a practical and convenient method for synthesizing β-lactones.

Classical methods for β-lactone synthesis include internal nucleophilic displacement of halide ion from β-halocarboxylate salts and the cycloaddition of aldehydes and ketones with ketenes. Alternative methods of β-lactone synthesis include halolactonization of β,γ-unsaturated carboxylic acids, deaminative cyclization of β-amino acids, the photocyclization of cinnamic acids, the photooxidation of 2-alkoxyoxetanes, and the palladium catalyzed carbonylation of halohydrins [H. E. Zaugg *Organic Reactions*, 8, 305–363 (1954); G. Searles in *Comprehensive Heterocyclic Chemistry*; A. R. Katritzky and C. W. Rees Eds.; Pergamon: Oxford, 1984; Vol. 7, Chapter 5.13]. W. Adam et al. describe a process for converting β-hydroxy carboxylic acids to β-lactones by treatment with benzenesulfonyl chloride in pyridine at subambient temperatures [W. Adam et al., *J. Am. Chem. Soc.* 94, 2000–2006 (1972)].

Wemple reported in 1975 [J. Wemple, *Tetrahedron Lett.* 3255–3258 (1975)] that lithium enolate derivatives of thiol esters add to aldehydes and ketones at −78° C. to yield, after quenching at −78° C., β-hydroxy thiol esters. Masamune reported that β-hydroxy thiol esters can be cyclized to form β-lactones by treatment with mercury (II) methanesulfonate, which is an expensive and toxic reagent [S. Masamune et al., *J. Am. Chem. Soc.* 98, 7874–5 (1976)]. Two examples of the "spontaneous" cyclization of thiol ester-ketone adducts to form β-lactones have been described [D. Seebach and R. Haner *Chemistry Lett.* 49–52 (1987) and J. Wemple et al. *J. Org. Chem.* 40, 3173–8 (1975)]. However, both of these cases involve unusual functionalized thiol esters, and in each case the β-lactones were formed as minor by-products of the reaction of main interest.

β-Lactones are important synthetic intermediates which can efficiently and conveniently be converted into other organic functional groups. In particular, β-lactones are easily transformed into alkenes under mild conditions. The alkene functional group is incorporated in the structure of numerous compounds with commercial importance such as pharmaceuticals, agricultural chemicals, flavor and fragrance compounds, etc. The development of a more convenient and efficient method for the synthesis of alkenes greatly facilitates the preparation of compounds whose structures incorporate the alkene functional group.

SUMMARY OF THE INVENTION

The present invention relates to a method of synthesizing β-lactones in which a thiol ester compound and a selected ketone or aldehyde are combined in the presence of a base under conditions appropriate for the reaction of the thiol ester and ketone or aldehyde to occur, and for the resulting adduct to undergo direct cyclization to a β-lactone. It further relates to the preparation of alkenes (olefins) by means of a two-step process, in which the β-lactone is converted to the corresponding alkene; a method of preparing alkenes in this manner is also the subject of the present invention.

In the method of producing β-lactones of the present invention, a thiol ester compound, a ketone or aldehyde, a base, and an organic solvent are combined, under conditions appropriate for reaction of the thiol ester and the ketone or aldehyde to occur. This reaction produces β-lactones in high yields, and the resulting β-lactones can then be further processed to stereospecifically produce the corresponding alkene. The method is useful to produce β-lactones, which are intermediates in the preparation of many commercially important compounds, and are important monomers for the synthesis of a variety of polymers. β-Lactones produced by the present method are used for the efficient synthesis of mono-, di-, tri, and tetrasubstituted alkenes, and for the stereoselective synthesis of di-, tri, and tetrasubstituted alkenes. The alkene functional group is incorporated in the structures of numerous commercially important compounds.

DETAILED DESCRIPTION OF THE INVENTION

The present invention relates to a new method for the synthesis of a class of compounds called β-lactones. The method involves combining a thiol ester compound and a ketone or an aldehyde at a low temperature, to form an adduct, and cyclization of this adduct (generally upon warming) to form the corresponding β-lactone. In an optional second step, the β-lactones formed are subjected to heat and/or catalysis, which results in decarboxylation of the β-lactone to produce alkenes (olefins). In conjunction with the present improved method of β-lactone synthesis, this two-step protocol provides a convenient and efficient new method for preparing alkenes.

Figure 1:
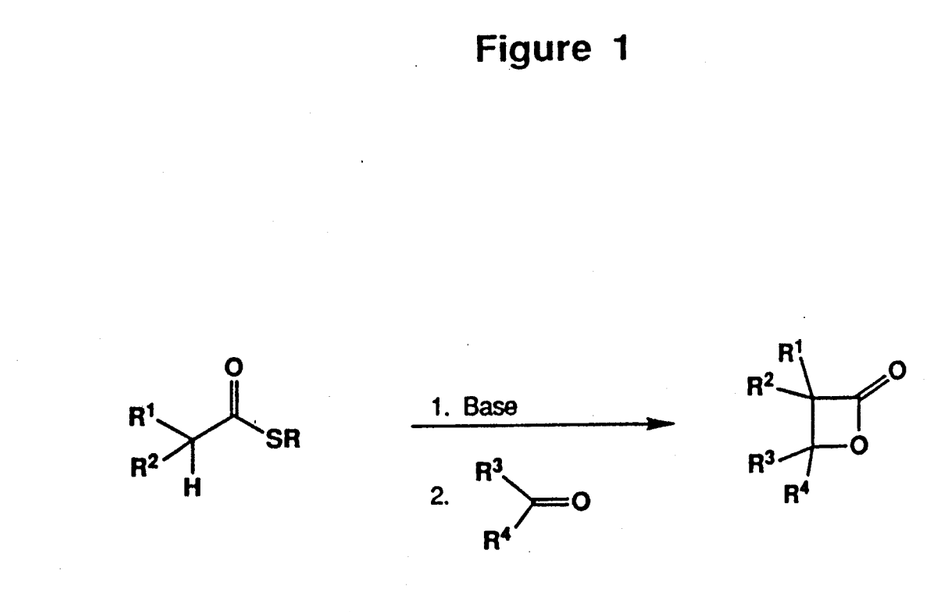
FIG. 1 is a schematic representation of the synthesis of β-lactones from a thiol ester and a ketone or aldehyde which is carried out by the method of the present invention.

The first step of the method of the present invention is represented by the scheme illustrated in FIG. 1. According to the method, a selected thiol ester is combined with a selected ketone or aldehyde, a base, and a solvent to produce a β-lactone. The thiol ester compounds which are used in the present process are compounds having the general formula:

wherein $R^1$ and $R^2$ are selected from the group consisting of: H, alkyl, aryl, alkenyl, and alkynyl; and wherein R is selected from the group consisting of aryl and alkyl. As used herein, the term alkyl group includes saturated, unsaturated, and functionalized carbon chains and rings having straight, branched, or cyclic configurations, including, for example, methyl, ethyl, isopropyl, and cyclohexyl groups. As used herein, the term aryl group encompasses any mono- or polycyclic aromatic ring system, including benzene, naphthalene, and heterocyclic aromatic ring systems such as pyridine and furan, as well as substituted derivatives of these aromatic and heteroaromatic ring systems. Examples of thiol ester compounds which can be used in the present reaction include S-phenyl 2-methylpropanethioate, S-phenyl propanethioate, and S-phenyl ethanethioate.

The thiol ester compound of choice is combined with a ketone having the following general formula:

wherein $R^3$ and $R^4$ are selected form the group consisting of: H, alkyl, aryl, alkenyl, alkynyl, or trialkylsilyl. As used herein, the term alkyl group includes saturated unsaturated, and functionalized carbon chains and rings having straight, branched, or cyclic configurations, including, for example, methyl, ethyl, isopropyl, and cyclohexyl groups. As used herein, the term aryl group encompasses any mono- or polycyclic aromatic ring system including benzene, naphthalene, and heterocyclic aromatic ring systems such as pyridine and furan, as well as substituted derivatives of these aromatic and heteroaromatic ring systems. Trialkylsilyl groups can include, for example, trimethylsilyl, triethylsilyl, or tert-butyldimethylsilyl. Examples of ketones which can be used in the present reaction include 4-phenylbutan-2-one, cyclohexanone, 1-cyclohexyl-1-ethanone, 6-methyl-5-hepten-2-one, and 1-tert-butyldimethylsilyl-1-ethanone.

Alternatively, aldehydes having the general formula:

can be used in lieu of ketones in the present reaction, wherein $R^3$ can be as described previously for the ketones. Aldehydes which can be used in the present reaction include octanal and cyclohexanecarboxaldehyde.

The reaction is generally carried out in the presence of a base. Bases which are useful in the present method are bases capable of deprotonating the thiol ester compound, without powerful nucleophilic action, and without promoting undesirable self-condensation reactions. Bases which provide these characteristics include metal amides (e.g., lithium amides), alkoxide bases (e.g., potassium tert-butoxide) and metal hydrides (e.g., NaH, KH). Metal amides are preferred bases for the present reaction. Metal dialkylamides, such as lithium diisopropylamide, are particularly preferred. The purpose of the base is to generate the enolate derivative of the thiol ester. Other methods of providing the enolate derivative, including from other precursors, can also be used for the present method.

The reaction is generally carried out in an organic solvent, including any standard ethereal organic solvent such as tetrahydrofuran (THF), dimethoxyethane, dioxane, and diethyl ether. THF is a particularly useful solvent for the present reaction. A mixture of solvents can also be used.

The present reaction is carried out at a temperatures such as to allow addition of the thiol ester compound to the ketone or aldehyde component. This will generally be from about −80° C. to about −30° C. Once the addition reaction is complete, the temperature is generally allowed to rise, thereby effecting the cyclization of the adduct to form the β-lactone. In some cases, cyclization can be accomplished without warming. Depending on the reactants used, however, the reaction mixture is generally allowed to warm to between −50° C. and 0° C.

The present method is usually performed according to the following general procedure: a solution of the base in the selected solvent in an appropriate reaction vessel is cooled to the desired temperature, the thiol ester compound is added, and reacts with the base, thereby forming the enolate derivative of the thiol ester. The ketone (or aldehyde) is then added to the thiol ester enolate, and the mixture is stirred for a sufficient time to allow the addition reaction between the thiol ester and ketone or aldehyde to occur. The reaction mixture is then allowed to warm for a period of time, and to a temperature, which permits cyclization of the adduct to occur to form the β-lactone. The β-lactone formed has the following general formula:

wherein $R^1$, $R^2$, $R^3$, and $R^4$ are as described above for the thiol ester and ketone or aldehyde reactants. Yields of up to 95% β-lactone have been obtained using the present process. Table 1 lists several β-lactones which were prepared by the present process.

TABLE 1
Preparation of β-Lactones via Thiol Esters:

| carbonyl compound | thiol ester | β-lactone | % yield |
|---|---|---|---|
| cyclohexanone | CH₃C(O)SPh | spiro β-lactone (cyclohexane) | 86 |
| cyclohexanone | CH₃CH₂C(O)SPh | spiro β-lactone with CH₃ | 95 |
| cyclohexanone | (CH₃)₂CHC(O)SPh | spiro β-lactone with two CH₃ | 87 |
| cyclohexyl methyl ketone | CH₃CH₂C(O)SPh | β-lactone (two diastereomers, C₆H₁₁, CH₃, CH₃) | 75 47:1 (isolated) 17:1 (crude) |
| PhCH₂CH₂C(O)CH₃ | (CH₃)₂CHC(O)SPh | β-lactone (CH₃, CH₃, CH₃, PhCH₂CH₂) | 62 |
| CH₃C(O)Sit-BuMe₂ | CH₃C(O)SPh | β-lactone (CH₃, t-BuMe₂Si) | 70 |
| n-C₇H₁₅CHO | (CH₃)₂CHC(O)SPh | β-lactone (CH₃, CH₃, n-C₇H₁₅) | 38 |

All reactions were performed under the following conditions: addition of thiol ester to ketone using LDA as base, at −78° C. for 30 min in THF; warming from −78 to ca. 0° C. over ca. 2 hours to cause cyclization to β-lactone.

Figure 2:
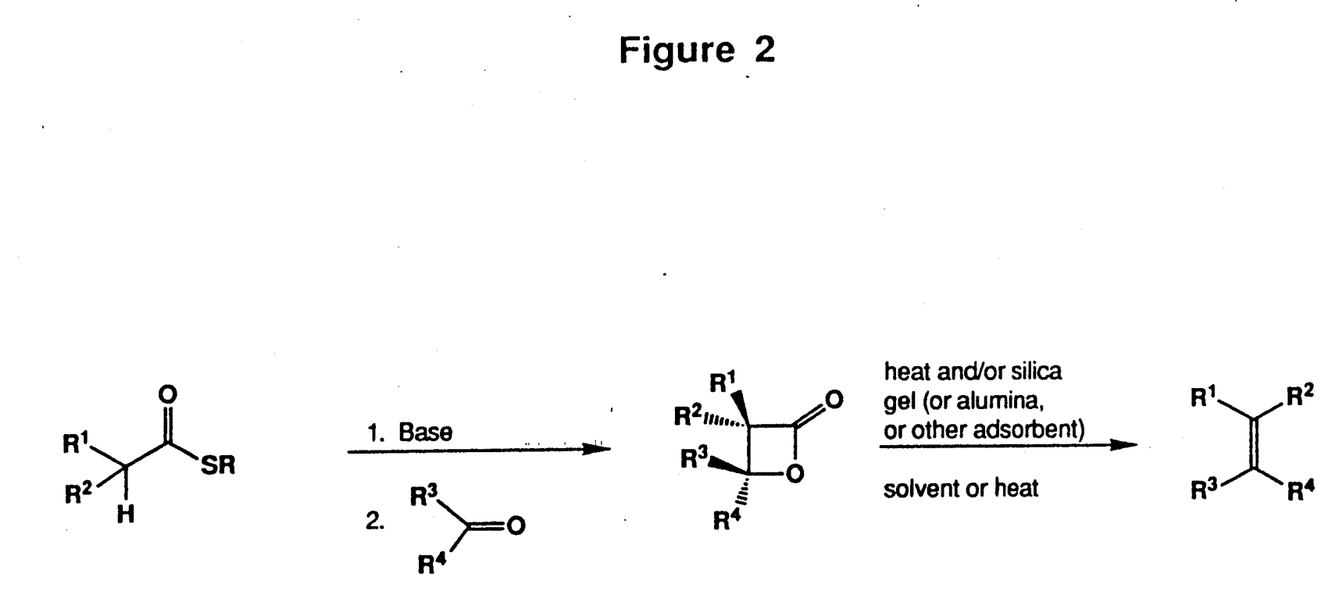
FIG. 2 is a schematic representation of the present two-step protocol in which a β-lactone is produced and then converted to an alkene, according to the method of the present invention.
Figure 3:
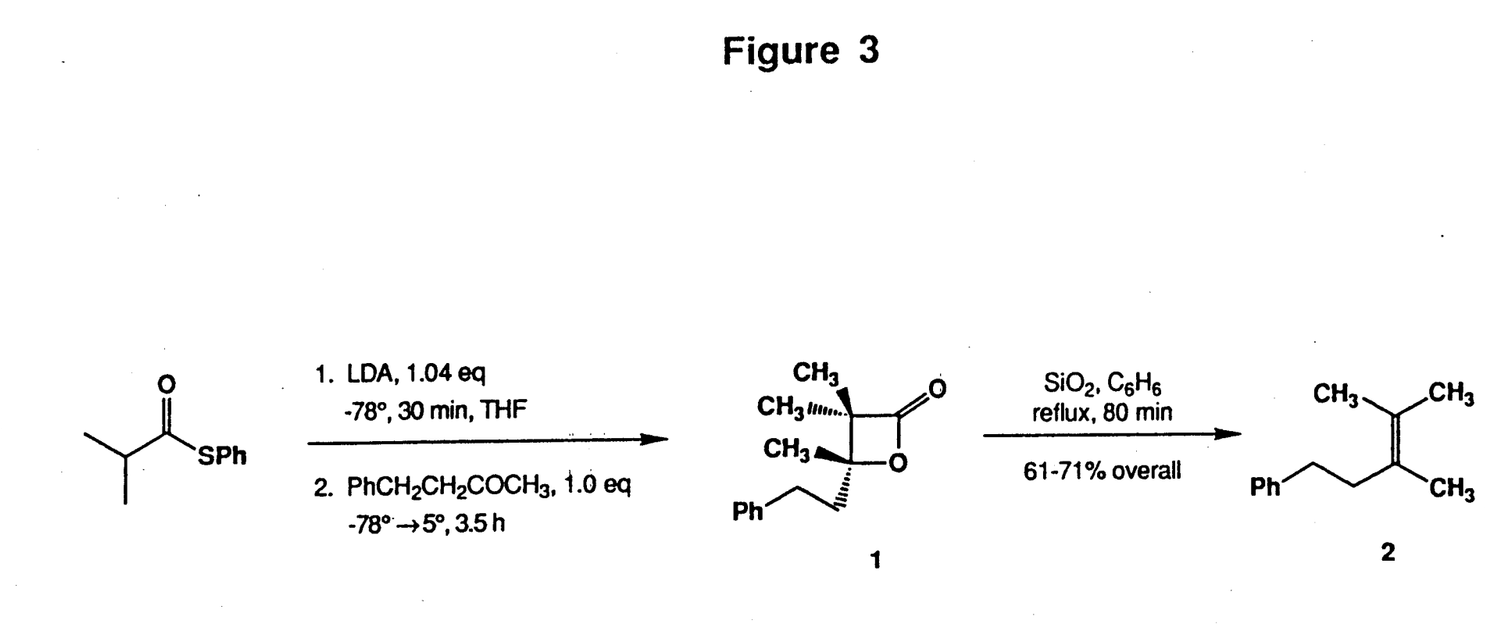
FIG. 3 shows the reaction of S-phenyl-2-methyl propanethioate with 4-phenylbutan-2-one to form 4-(2-phenylethyl)-3,3,4-trimethyloxetan-2-one (1), which was then heated in the presence of silica gel to form 2,3-dimethyl-5-phenyl-2-pentene (2).

It is well known that heating β-lactones results in decarboxylation to produce alkenes. In conjunction with the present method of β-lactone synthesis, a two-step process is provided to produce alkenes. This two-step process is set forth in FIG. 2. The first step is the preparation of the β-lactone, as set out in the previous section. In the second step, the β-lactone is converted to the corresponding alkene. This second step is generally carried out by first adding an adsorbent such as silica gel or alumina and a solvent to an appropriate reaction vessel. Solvents which are preferred for the reaction include methylene chloride, benzene, toluene, hexane, diethyl ether, cyclohexane, petroleum ether, isooctane, chloroform, and carbon tetrachloride. Alternatively, the reaction may be carried out in the absence of a solvent. This variation in the procedure is preferred when the alkene product has a low boiling point, and separation from solvent would be difficult. In some cases the reaction can be carried out without the addition of an adsorbent, with or without solvent. This variation in the procedure is preferred when the substitutents on the β-lactone ring contain functional groups which are unstable in the presence of the adsorbents. The β-lactone is then added to the reaction vessel. The reaction mixture is then heated until the decarboxylation reaction is complete, and then allowed to cool to room temperature. In some cases the reaction proceeds without heating. The reaction can be carried out at a temperature of from about 25° C. to about 150° C. The product of this second step is an alkene having the general formula:

wherein $R^1$, $R^2$, $R^3$, and $R^4$ correspond to the groups present on the β-lactone starting material. An example of the present two-step process for producing alkenes is schematically illustrated in FIG. 3.

The present two-step process allows for the stereoselective synthesis of di-, tri-, and tetrasubstituted alkenes. That is, a specific alkene stereoisomer can be produced by the present method. One embodiment of the method for the stereoselective synthesis of alkenes is set forth in FIG. 2, wherein $R^2$ is H, and $R^1$, $R^3$, and $R^4$ are as defined as above, except that $R^3$ is more sterically demanding than $R^4$. Thus, in one particular embodiment of the present method, illustrated in FIG. 4, the thiol ester wherein $R^1$ is methyl and $R^2$ is H, is combined with the ketone in which $R^3$ is cyclohexyl and $R^4$ is methyl, according to the conditions described above for the addition of thiol esters to ketones, to produce the β-lactone as a mixture of diastereomers 3 and 4 in the ratio of 17:1, which can be increased to 47:1 by recrystallization from pentane.

Figure 4:
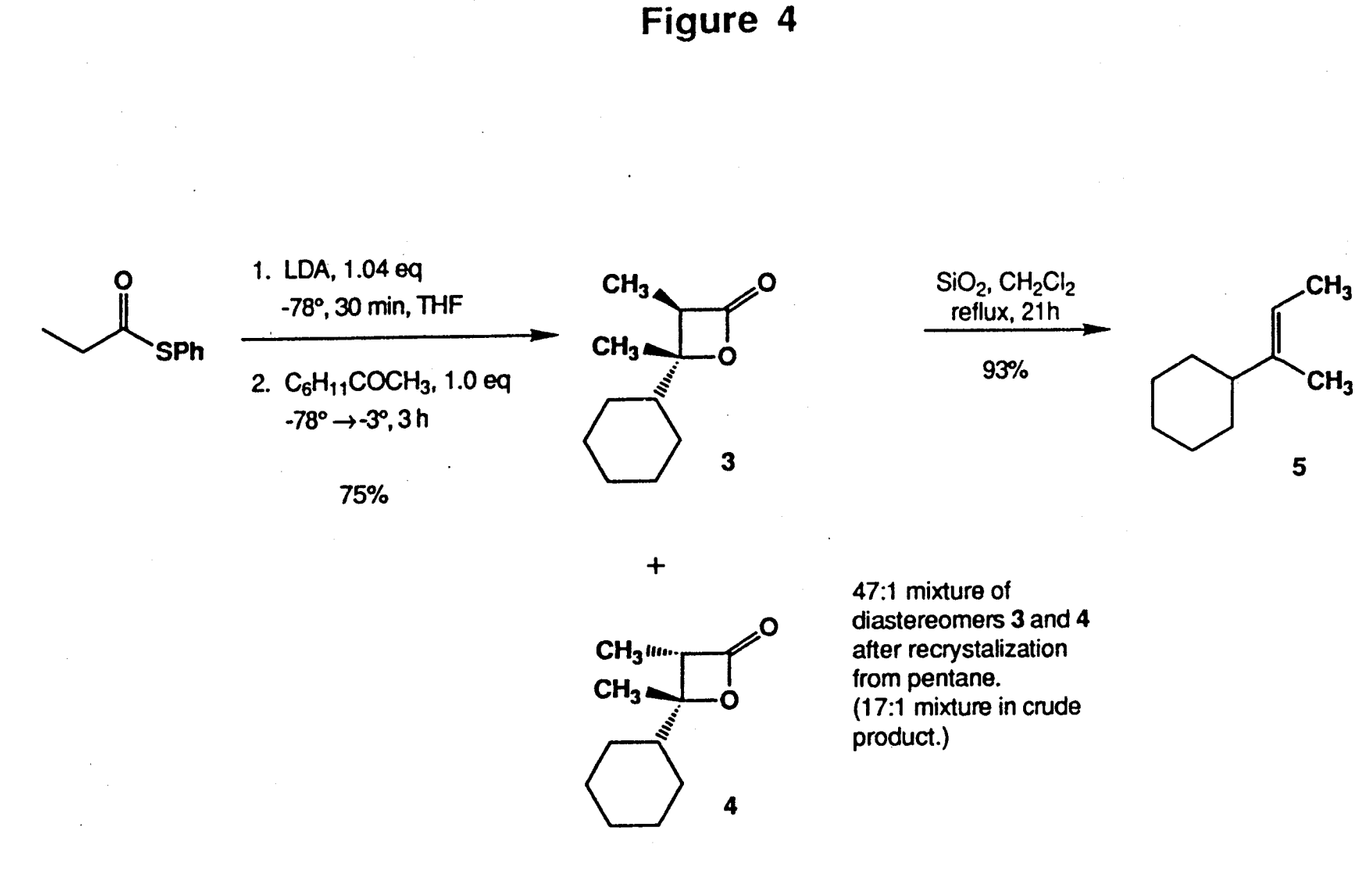
FIG. 4 shows the reaction of S-phenyl propanethioate with 1-cyclohexyl-1-ethanone to form 4-cyclohexyl-3,4-dimethyloxetan-2-one (3), which was then heated in the presence of silica gel to form 2-cyclohexyl-2-butene.

The β-lactone 3 is then converted to the trisubstituted alkene 5 using the conditions described above for the decarboxylation of β-lactones. The decomposition of the β-lactone to alkene is a stereospecific process, and thus the stereoselective synthesis of β-lactones according to the present method also constitutes a new stereoselective synthesis of substituted alkenes.

The β-lactones produced by the present method are useful as building blocks for the synthesis of other classes of organic compounds. The ring strain contained in this four-membered heterocycle imparts to these compounds the property of readily undergoing ring opening upon reaction with nucleophilic reagents. For example, β-lactones undergo hydrolysis to form β-hydroxy acids, and can be treated with ammonia and amines to yield either β-hydroxy amides or β-amino carboxylic acids. In addition, the β-lactone ring is incorporated in the structure of a number of biologically-active natural products including anisatin, neoanisatin, esterastin, and antibiotic 1233A. β-Lactones undergo both cationic and anionic polymerization to produce useful polyesters such as poly-BCMO. β-Lactones have also been used as cross-linking agents to help protect cotton, wool, and wood against attack by bacteria, molds, and insects [G. Searles in *Comprehensive Heterocyclic Chemistry*; A. R. Katrizky and C. W. Rees Eds.; Pergamon: Oxford, 1984; Vol. 7, Chapter 5.13].

The present method is also useful for the synthesis of mono-, di-, tri-, and tetrasubstituted alkenes, and for the stereoselective synthesis of substituted alkenes. An enormous diversity of commercially important compounds incorporate the alkene functional group in their structures. Representative compounds of interest include pharmaceuticals, agricultural chemicals, and flavor and fragrance compounds. In many cases, only one stereoisomer of an alkene exhibits the desired properties, and the efficient synthesis of the compound requires a stereoselective method for the formation of the carbon-carbon double bond.

The invention is further illustrated by the following examples, which are not to be taken as limiting in any way.

EXAMPLES

EXAMPLE 1

Prepration of 4-(2-Phenylethyl)-3,3,4-trimethyloxetan-2-one (1).

A 100-mL, three-necked, round-bottomed flask equipped with an argon inlet adapter, rubber septum, thermometer, and magnetic stirring bar was charged with 50 mL of tetrahydrofuran (THF) and diisopropylamine (0.77 mL, 5.5 mmol), and then cooled in an ice bath while n-butyllithium solution (1.63M in hexanes, 3.19 mL, 5.2 mmol) was added rapidly via syringe. After 15 min, the ice bath was replaced with a dry ice-acetone bath (−78° C.), and S-phenyl 2-methylpropanethioate (0.901 g, 5.00 mmol) was added dropwise via syringe over the course of ca. 30 seconds. After 30 min, 4-phenylbutan-2-one (0.741 g, 5.0 mmol) was added dropwise via syringe over the course of ca. 30 seconds. The reaction mixture was stirred at −78° C. for 30 minutes and then allowed to warm to −14° C. over the course of 2 h. Half-saturated NH$_4$Cl solution (50 mL) was then added, and the resulting mixture was partitioned between 50 mL of water and 75 mL of diethyl ether. The organic phase was extracted with two 75-mL portions of 10% potassium carbonate (K$_2$CO$_3$) solution, 75 mL of saturated sodium (NaCl) solution, dried over magnesium sulfate (MgSO$_4$), filtered, and concentrated to afford 1.203 g of a pale yellow oil. Low temperature (−78° C.) recrystallization from pentane, followed by filtration of an ether solution, concentration, recrystallization (−78° C.) twice more from pentane, and trituration with pentane (0° C.) afforded 0.672 g (62%) of 1 as a white crystalline solid: mp 51.5°–55.5° C.; IR (CHCl$_3$) 3084, 3062, 3022, 2986, 2934, 2868, 1811, 1604, 1497, 1477, 1464, 1394, 1383, 1298, 1293, 1174, 1144, 1115, 1074, 1042, 960, 818, and 702 cm$^{-1}$; $^1$H NMR (300 MHz, CDCl$_3$) δ 7.31 (appar. t, J=7.1 Hz, 2H), 7.19–7.24 (m, 3H), 2.63–2.77 (m, 2H), 1.99–2.21 (m, 2H), 1.57 (s, 3H), and 1.35 (s, 6H); $^{13}$C NMR (75 MHz, CDCl$_3$) δ 175.7, 141.3, 128.7, 128.3, 126.4, 84.9, 54.8, 38.5, 30.4, 20.0, 19.1, and 18.2; Anal. Calcd for C$_{14}$H$_{18}$O$_2$: C, 77.03; H, 8.31. Found: C, 77.23; H, 8.49.

EXAMPLE 2

Preparation of 2,3-Dimethyl-5-phenyl-2-pentene (2).

A 25-mL, two-necked, round-bottomed flask equipped with an argon inlet adapter, rubber septum, and magnetic stirring bar was charged with 10 mL of tetrahydrofuran (THF) and diisopropylamine (0.154 mL, 1.10 mmol), and then cooled in an ice bath while n-butyllithium solution (1.63M in hexanes, 0.64 mL, 1.04 mmol) was added rapidly via syringe. After 15 min, the ice bath was replaced with a dry ice-acetone bath (−78° C.), and S-phenyl 2-methylpropanethioate (0.180 g, 1.00 mmol) was added dropwise via syringe over the course of ca. 15 seconds. After 30 min, 4-phenylbutan-2-one (0.148 g, 1.00 mmol) was added dropwise via syringe over the course of ca. 15 seconds. The reaction mixture was stirred at −78° C. for 30 minutes and then allowed to warm to 5° C. over the course of 3 h. Half-saturated ammonium chloride (NH$_4$Cl) solution (10 mL) was then added, and the resulting mixture was partitioned between 10 mL of water and 20 mL of diethyl ether. The organic phase was extracted with two 20-mL portions of 10% potassium carbonate (K$_2$CO$_3$) solution, 20 mL of saturated sodium chloride (NaCl) solution, dried over magnesium sulfate (MgSO$_4$), filtered, and concentrated to afford 0.238 g of a yellow oil.

A 25-mL, one-necked, round-bottomed flask equipped with a magnetic stirring bar and a cold-finger condenser fitted with an argon inlet adapter was charged with 0.50 g of 230–400 mesh J. T. Baker #7024 silica gel. The flash was evacuated and then filled with argon, and a solution of the product of the previous reaction in 10 mL of benzene was added. The reaction mixture was refluxed for 80 minutes and then allowed to cool to room temperature and filtered. The residue was washed with an additional 5 mL of benzene, and the combined filtrates were concentrated to afford 0.192 g of yellow oil. Column chromatography on silica gel (elution with hexanes) afforded 0.107 g (61%) of 2 as a colorless oil: IR (film) 3086, 3062, 3026, 2988, 2918, 2856, 1606, 1596, 1454, 1373, 1185, 1155, 1071, 1029, 749, and 698 cm$^{-1}$; $^1$H NMR (300 MHz, CDCl$_3$) δ 7.23–7.29 (m, 2H), 7.14–7.19 (m, 3H), 2.64 (appar. t, J=8.1 Hz, 2H), 2.31 (appar. t, J=8.1 Hz, 2H), 1.67 (s, 3H), 1.64 (s, 3H), and 1.58 (s, 3H); $^{13}$C NMR (75 MHz, CDCl$_3$) δ 142.9, 128.6, 128.4, 127.1, 125.8, 124.9, 36.6, 34.5, 20.3, 19.7, and 18.2; Anal. Calcd for C$_{13}$H$_{18}$: C, 89.59; H, 10.41. Found: C, 89.62; H, 10.61.

EXAMPLE 3

Stereoselective Preparation of r-4-Cyclohexyl-t-3,4-dimethyloxetan-2-one (3) and r-4-Cyclohexyl-c-3,4-dimethyloxetan-2-one (4).

A 25-ml, two-necked, round-bottomed flask equipped with an argon inlet adapter, rubber septum, and magnetic stirring bar was charged with 10 mL of tetrahydrofuran (THF) and diisopropylamine (0.154 mL, 1.10 mmol), and then cooled in an ice bath while n-butyllithium solution (1.63M in hexanes, 0.64 mL, 1.04 mmol) was added rapidly via syringe. After 15 min, the ice bath was replaced with a dry ice-acetone bath (−78° C.), and S-phenyl propanethioate (0.166 g, 1.00 mmol) was added dropwise via syringe over the course of ca. 15 seconds. After 30 min, 1-cyclohexyl-1-ethanone (0.126 g, 1.00 mmol) was added dropwise via syringe over the course of ca. 15 seconds. The reaction mixture was stirred at −78° C. for 30 minutes and then allowed to warm to −3° C. over the course of 2.5 h. Half-saturated ammonium chloride (NH$_4$Cl) solution (10 mL) was then added, and the resulting mixture was partitioned between 10 mL of water and 20 mL of diethyl ether. The organic phase was extracted with two 20-mL portions of 10% pottassium carbonate (K$_2$CO$_3$) solution, 20 mL of saturated sodium chloride (NaCl) solution, dried over magesium sulfate (MgSO$_4$), filtered, and concentrated to afford 0.196 g of a yellow oil. Low temperature (3178° C.) recrystallization twice from pentane afforded 0.136 g (75%) of a mixture of 3 and 4 as a pale yellow oil (47:1 mixture of isomers as determined by $^1$H NMR analysis): IR (film) 2986, 2930, 2860, 1818, 1465, 1453, 1388, 1334, 1263, 1250, 1217, 1177, 1165, 1129, 1113, 1080, 1057, 1031, 997, 947, 895, 853, 843, 809, 800, and 778 cm$^{-1}$; $^1$H NMR (300 MHz, CDCl$_3$) 3: δ 3.31 (q,J=7.7 Hz, 1H), 1.77-189 (m, 3H), 158-1.77 (m, 3H), 136 (s, 3H), 1.25 (d,J=7.7 Hz, 3H), and 0.93-1.32 (m, 5H); 4 (partial data): δ 3.87 (q); $^1$H NMR NOE experiment: irradiation of 3 at δ 3.31 produced an enhancement at δ 1.8-1.9 and 1.6-1.7; $^{13}$C NMR (75 MHz, CDCl$_3$) δ172.7, 84.3, 51.0, 47.9, 27.0, 26.4, 25.9, 25.5, 15.7, and 9.0; Anal. Calcd for C$_{11}$H$_{18}$O$_2$: C, 72,49; H, 9.95. Found: C, 72.64; H, 10.06.

EXAMPLE 4:

Stereoselective Preparation of (E)-2-Cyclohexyl-2-butene (5).

A 10-mL, one-necked, round-bottomed flask equipped with a magnetic stirring bar and a cold-finger condenser fitted with an argon inlet adapter was charged with 0.160 g of 230–400 mesh J. T. Baker #7024 silica gel. The flask was evacuated and then filled with argon, and a solution 0.080 g (0.44 mmol) of the product of the previous reaction in 3 mL of methylene chloride (CH$_2$Cl$_2$) was added. The reaction mixture was refluxed for 21 hours and then allowed to cool to room temperature and filtered. The residue was washed with an additional 3 mL of methylene chloride, and the combined filtrates were concentrated to afford 0.057 g (93%) of 5 as a colorless oil: IR (film) 2922, 2852, 2662, 1716, 1667, 1449, 1381, 1349, 1338, 1262, 1216, 1216, 1200, 1178, 1144, 1097, 1041, 1020, 999, 957, 930, 895, 854, 817, 759, 747, and 689 cm$^{-1}$; $^1$H NMR (300 MHz, CDCl$_3$) .16–521 (m, 1H), 1.57 (s, 3H), 1.57 (s, 3H), 156 (d,J=4 Hz, 3H), 144–186 (m, 6H), and 1.06-1.32 (m, 5H); $^{13}$C NMR (75 MHz, CDCl$_3$) δ 141.2, 116.1, 47.3, 32.0, 26.8, 26.5, 140.0, and 13.3.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by following claims.

We claim:

1. A method for producing a β-lactone comprising: combining a thiol ester having the general formula:

wherein R$_1$ and R$_2$ are selected from the group consisting of: H, alkyl, aryl, alkenyl and alkynyl groups; and wherein R is selected from the group consisting of alkyl and aryl groups; with a ketone or aldehyde, a base and a solvent under conditions sufficient to cause addition of the thiol ester to the ketone or aldehyde to form an adduct, and subsequent cyclization of the adduct to form the corresponding β-lactone.

2. A method of claim 1, wherein R is phenyl.

3. A method of claim 1, wherein R$^1$ and R$^2$ are both methyl.

4. A method of claim of claim 1 wherein the ketone is a compound having the general formula:

wherein R$^3$ and R$^4$ are selected from the group consisting of: alkyl, aryl, alkenyl, alkynyl and trialkylsilyl.

5. A method of claim 4, wherein the R$^3$ is methyl and R$^4$ is cyclohexyl.

6. A method of claim 1, wherein the aldehyde is a compound having the general formula:

wherein R³ is selected from the group consisting of H, alkyl, aryl, alkenyl, alkynyl, and trialkylsilyl.

7. A method of claim 1, wherein the base is selected from the group consisting of metal amides, dialkyl amides, alkoxides, and metal hydrides.

8. A method of claim 1, wherein the base is a metal amide.

9. A method of claim 8, wherein the metal amide is lithium diisopropylamide.

10. A method of producing a β-lactone having the general formula:

wherein R¹ and R² are selected from the group consisting of: H, alkyl, aryl, alkenyl, and alkynyl; wherein R³ and R⁴ are selected from the group consisting of: alkyl, aryl, alkenyl, alkynyl and trialkylsilyl; comprising the steps of: combining a thiol ester having the general formula:

wherein R is selected from the group consisting of: aryl and alkyl; with a ketone having a general formula:

a base, and a solvent, under conditions appropriate to produce the β-lactone.

11. A method of claim 10 wherein R is phenyl, R¹ and R² are H, and wherein R³ and R⁴ together form a pentamethylene chain.

12. A method of claim 10, wherein R is phenyl, R' is H, R² is CH₃ and R³ and R⁴ together form a pentamethylene chain.

13. A method of claim 10, wherein R' and R² are CH₃ and R³ and R⁴ together form a pentamethylene chain.

14. A method of claim 10, wherein R is phenyl, R¹ and R² are H, R³ is CH₃, and R⁴ is PhCH₂CH₂.

15. A method for producing alkenes comprising the steps of:
  a. combining a thiol ester with a ketone or aldehyde, a base, and a solvent, under conditions appropriate to form a β-lactone having the general formula:

wherein R¹ and R² are selected from the group consisting of: H, alkyl, aryl, alkenyl, and alkynyl; and R³ and R⁴ are selected from the group consisting of: alkyl, aryl, alkenyl, alkynyl and trialkylsilyl; and
  b. converting the β-lactone produced in step (a) to an alkene having the general formula:

wherein R¹, R², R³ and R⁴ are as defined above.

16. A method of claim 15 wherein step (b) further comprises contacting the β-lactone with a catalyst.

17. A method of claim 16, wherein the catalyst is silica gel or alumina.

18. A method of stereoselectively producing a substituted alkene having the general formula:

wherein R¹ and R² are selected from the group consisting of: H, alkyl, aryl, alkenyl, and alkynyl, and R³ and R⁴ are selected from the group consisting of: alkyl, aryl, alkenyl, alkynyl and trialkylsilyl, and wherein R² is more sterically demanding than R¹ and R³ is more sterically demanding than R⁴, comprising the steps of:
  a. combining a thiol ester having the general formula:

where R is selected form the group consisting of aryl and alkyl; with a ketone or aldehyde having the general formula:

respectively, a base, and a solvent, under conditions sufficient to produce the β-lactone; and
  b. converting the β-lactone produced in step (a) to the substituted alkene.

19. A method of claim 18, wherein step (b) further comprises contacting the β-lactone with a catalyst.

20. A method of stereoselectively producing a trisubstituted alkene having the general formula:

wherein R¹ is H, R² is selected from the group consisting of: alkyl, aryl, alkenyl, and alkynyl, and R³ and R⁴ are selected from the group consisting of alkyl, aryl, alkenyl, alkynyl, and trialkylsilyl, and wherein R³ is more sterically demanding than R⁴, comprising the steps of:

a. combining a thiol ester having the general formula:

wherein R is selected from the group consisting of: aryl and alkyl; with a ketone having the general formula:

a base, and a solvent, under conditions sufficient to produce the β-lactone; and b. converting the β-lactone produced in step (a) to the trisubstituted alkene.

21. A method of claim 20, wherein step (b) further comprises contacting the β-lactone with a catalyst.

22. A method for producing a β-lactone comprising: contacting an enolate derivative of a thiol ester having the general formula:

wherein R¹ and R² are selected from the group consisting of: H, alkyl, aryl, alkenyl and alkynyl groups; and wherein R is selected from the group consisting of alkyl and aryl; with a ketone or aldehyde and a solvent under conditions sufficient to cause addition of the thiol ester enolate to the ketone or aldehyde to form an adduct, and subsequent cyclization of the adduct to form the β-lactone.

23. A method of claim 22 comprising reacting a lithium enolate of the thiol ester with a ketone or aldehyde.

24. A method of claim 22 further comprising converting the β-lactone to an alkene.

* * * * *